(12) United States Patent (10) Patent No.: US 7,518,730 B2
Yates et al. (45) Date of Patent: Apr. 14, 2009

(54) APPARATUS AND METHOD FOR CHEMICAL SENSING

(75) Inventors: Stephen Yates, Arlington Heights, IL (US); Glen Sanders, Scottsdale, AZ (US)

(73) Assignee: Honeywell International Inc., Morristown, NJ (US)

( * ) Notice: Subject to any disclaimer, the term of this patent is extended or adjusted under 35 U.S.C. 154(b) by 92 days.

(21) Appl. No.: 11/679,454

(22) Filed: Feb. 27, 2007

(65) Prior Publication Data

US 2008/0204758 A1 Aug. 28, 2008

(51) Int. Cl.
*G01B 9/02* (2006.01)
(52) U.S. Cl. ...................................... 356/480
(58) Field of Classification Search ................ 356/477, 356/478, 480, 481, 483; 385/12, 141, 144
See application file for complete search history.

(56) References Cited

U.S. PATENT DOCUMENTS

| | | | |
|---|---|---|---|
| 4,834,496 A | 5/1989 | Blyler, Jr. et al. | |
| 5,248,319 A | 9/1993 | Ekiner et al. | |
| 5,591,250 A | 1/1997 | Stern et al. | |
| 5,649,045 A | 7/1997 | Fjare et al. | |
| 5,779,763 A * | 7/1998 | Pinnau et al. | 95/39 |
| 6,694,067 B1 * | 2/2004 | O'Keefe et al. | 385/12 |
| 2008/0116361 A1 * | 5/2008 | Sanders et al. | 250/227.18 |

FOREIGN PATENT DOCUMENTS

WO WO 2005/113121 12/2005

OTHER PUBLICATIONS

Alexander Star, Tzong-Ru Han, Vikram Joshi, Joseph R. Stetter, Sensing with Nafion Coated Carbon Nanotube Field-Effect Transistors, Electroanalysis 2004, 16, No. 1-2, pp. 108-112.

NB McKeown, B. Ghanem, K. J. Msayib, P. M. Budd, C. E. Tattershall, K. Mahmood, S. Tan, D. Book, H. W. Langmi and A. Walton, Towards polymer-based hydrogen storage materials: engineering ultramicroporous cavities within polymers of intrinsic microporosity, Angew. Chem. Int. Ed., 2006, 45, 1804-1807.

P.M. Budd, B. Ghanem, K. Msayib, N.B. McKeown, C. Tattershall, A nanoporous network polymer derived from hexaazatrinaphthylene with potential as an adsorbent and catalyst support, J. Mater. Chem., 2003, 13, 2721-26.

(Continued)

*Primary Examiner*—Michael A Lyons
(74) *Attorney, Agent, or Firm*—Husch Blackwell Sanders Welsh & Katz

(57) ABSTRACT

A chemical detector for detecting predetermined chemicals. The chemical detector includes an optical fiber and a polymer having a high fractional free volume higher than about 0.1 that clads a length of the optical fiber. The optical fiber is arranged within an optical resonator. The chemical detector further includes a coherent light source that excites the optical resonator and a chemical signature detector that detects a predetermined chemical based upon a change in a resonance attenuation or refractive index of the optical fiber caused by absorption of the predetermined chemical into the high intrinsic microporosity polymer cladding of the fiber.

19 Claims, 3 Drawing Sheets

OTHER PUBLICATIONS

NB McKeown, S. Hanif, K. Msayib, C. Tattershall, PM Budd, Porphyrin-based nanoporous network polymers, Chem. Commun., 2002, 2782-83.

NB McKeown, S. Makhseed, PM Budd, Phthalocyanine-based nanoporous network polymers, Chem. Commun., 2002, 2780-81.

PM Budd, NB McKeown, D. Fritsch, Free volume and intrinsic microporosity in polymers, J. Mater. Chem., 2005, 15, 1977-86.

PM Budd et al., Polymers of intrinsic microporosity (PIMs): robust, solution-processable, organic nanoporous materials, Chem. Commun., 2004, 230-31.

NB McKeown et al., "Polymers of Intrinsic Microporosity (PIMs): Bridging the Void between Microporous and Polymeric Materials," Chem. Eur. J., 2005, 11, 2610-20.

PM Budd et al., "Solution-Processed, Organophilic Membrane Derived from a Polymer of Intrinsic Microporosity," Adv. Mater., 2004, 16, 456-59.

PM Budd et al., "Gas Separation Membranes from Polymers of Intrinsic Microporosity," J. Membr. Sci., 2005, 251, 263-69.

N.B. McKeown et al., Towards Polymer-Based Hydrogen Storage Materials: Engineering Ultramicroporous Cavities within Polymers of Intrinsic Microporosity, Angew. Chem. Int. Ed. 2006, 45, 1804-07, Feb. 2006.

Y. Hirayama et al., Relation between Gas Permeabilities and Structure of Polyimides, in Polymer Membranes for Gas and Vapor Separation, B.D. Freeman, I. Pinnau, ed. (1999).

G. Houghham et al., Influence of Free Volume Change on the Relative Permittivity and Refractive Index in Fluoropolyimides, Macromolecules 29, 3453-56 (1996).

Y. Hirayama et al., Relation of gas permeability with structure of aromatic polyimides I, J. Membrane Sci. 111, 169-82 (1996).

* cited by examiner

APPARATUS AND METHOD FOR CHEMICAL SENSING

FIELD OF THE INVENTION

The present invention generally relates to environment sensing, and more particularly, to optical systems and methods for detecting the presence of chemical materials.

BACKGROUND OF THE INVENTION

In recent times, greater emphasis has been placed on national home security and detecting threats to populations. In particular, detecting or sensing the presence of undesired chemicals or biological material in the environment has become a priority, and a variety of detection devices have been developed in response thereto. One example is a chemical sensor that uses an optical fiber having a core and a cladding. The cladding, or coating on the cladding, has optical properties which are altered in the presence of a predetermined material to be detected. The amount of light transmitted through the core of the optical fiber is a function of the change in optical properties of the cladding or coating interacting with the material to be detected.

One design consideration for conventional detection devices is with sensitivity. In general, for a particular detection device, more time is generally required to detect the presence of undesired materials at lower concentration levels.

Accordingly, it is desirable to provide a sensor for detecting the presence of chemical and/or biological agents with enhanced sensitivity while minimizing the detection time. In addition, it is desirable to provide a sensor for detecting the presence of multiple and different threats while minimizing the package size of the sensor. Furthermore, other desirable features and characteristics of the present invention will become apparent from the subsequent detailed description of the invention and the appended claims, taken in conjunction with the accompanying drawings and this background of the invention.

SUMMARY

A chemical detector for detecting predetermined chemicals. The chemical detector includes an optical fiber, arranged in an optical resonator, and a polymer having a high fractional free volume higher than about 0.1 that clads a length of the optical fiber. The chemical detector further includes a coherent light source that excites the optical fiber and a chemical signature detector that detects a predetermined chemical based upon a change in the resonance line shape characteristics of the optical fiber resonator caused by absorption of the predetermined chemical into the high intrinsic microporosity polymer cladding of the fiber. Among the resonance characteristics that may be detected are the free spectral range (refractive index measurement), the linewidth (light attenuation measurement), and the magnitude of the peak or dip resonance (light attenuation measurement).

High fractional free volume polymers considered to be useful as or as a coating for cladding on the optical fiber and for detecting a predetermined chemical in accordance with the present invention are those having a fractional free volume higher than about 0.1, and in one embodiment of the invention preferably are polymers having empty regions within the polymer structure capable of being at least partially filled with a predetermined chemical to be detected. In another embodiment of the invention, the high fractional free volume polymer having a fractional free volume higher than about 0.1 is microporous. The cladding of the optical fiber can be applied by any of the methods known to the art.

BRIEF DESCRIPTION OF THE DRAWINGS

The present invention will hereinafter be described in conjunction with the following drawings figures, wherein like numerals denote like elements.

DETAILED DESCRIPTION OF A PREFERRED EMBODIMENT

The following detailed description of the invention is merely exemplary in nature and is not intended to limit the invention or the application and uses of the invention. Furthermore, there is no intention to be bound by any theory presented in the preceding background or the summary of the invention or the following detailed description of the invention.

Apparatus and methods are provided for sensing one or more chemical agents in an environment. In general, the apparatus comprises a resonator having an optical fiber coil with a cladding or coating that changes in absorbance or refractive index when exposed to a specific chemical contaminant. When an input light beam (e.g., from a light source) is supplied to the resonator and the input light beam is tuned to the resonance frequency of the optical fiber coil in one direction (e.g., a clockwise or a counter-clockwise direction of the optical fiber coil in the case of a ring resonator), a resonance lineshape is produced in the region of the resonance frequency, which is sensed by the light circulating through the resonator. With the agent to be detected absent from the environment, the resonance lineshape has a first (e.g., narrow) profile corresponding to a low energy loss of the light circulating in the resonator. With the presence of the predetermined chemical agent in the environment of the optical fiber coil, this agent is absorbed into the cladding and, as a result, a portion of the light circulating in the optical fiber coil is scattered or absorbed. The normally narrow resonance lineshape changes to a wider, shallower profile. This change in resonance lineshape represents a greater energy loss resulting from the scattered light or absorbed light and thus, indicates the presence of the predetermined chemical agent. Another resonance characteristic, more likely to be utilized for measurement in the case of a more "transparent" chemical agent (one that has less impact on optical attenuation), the free spectral range (frequency difference between resonances) will change, and may be measured. This is due to absorption of the chemical affecting the index of refraction experienced by the light. Multiple optical fiber coils may be multiplexed together in the sensor, forming multiple resonators, to simultaneously detect the presence of multiple chemical agents. The additional resonators may also be used to sense other secondary materials, whose presence may adversely bias the measurement of the primary material that is intended to be detected. In this way, cross-sensitivities of one resonator coil or indicator to a secondary material may be eliminated. This provides a clearer measurement of the primary material or eliminates the possibility of a false alarm that is caused by the secondary material.

Figure 1:
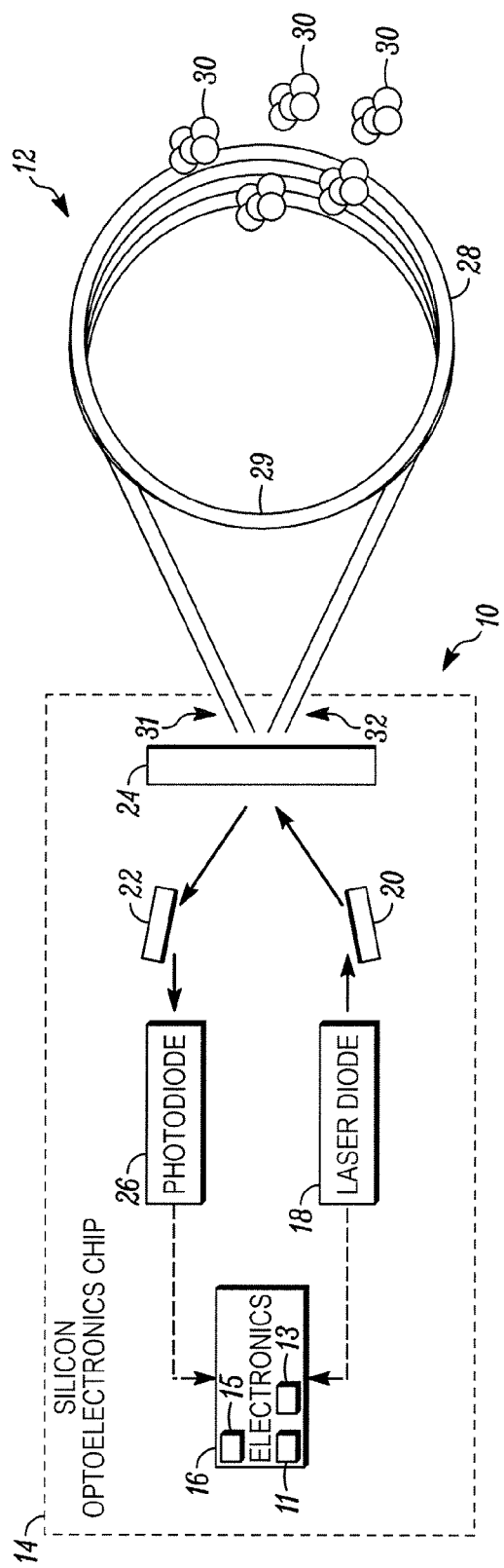
FIG. 1 is a schematic diagram of a chemical agent sensor in accordance with an illustrated embodiment of the invention.

Referring now to the drawings, FIG. 1 is a schematic diagram of a chemical agent sensor 10 in accordance with an exemplary embodiment of the present invention. The sensor 10 comprises a tunable coherent light source 18 (e.g., an external cavity a laser diode, a distributed feedback (DFB) laser diode, etc.), a first mirror reflector 20, a recirculator 24 (e.g., a highly reflective mirror with low, but non-zero transmittance), an optical fiber coil 28 having a first end 31 receiving light from the light source 18 via the first mirror reflector 20 and recirculator 24, a second mirror reflector 22 receiving a light output from a second end of the optical fiber coil 28 via the recirculator 24, a photodetector (e.g., a photodiode) 26, and an electronics module 16 coupled to the photodetector 26 and the light source 18. The input mirror 24 and optical fiber coil 28 together form a resonator 12. The resonator 12 may have a variety of configurations, and some exemplary embodiments are described herein. The light introduced to the resonator 12 is monochromatic and circulates through multiple turns of the optical fiber coil 28 using the recirculator 24. A light output from the resonator 12 is responsive to the absence or presence of a predetermined chemical agent 30. In some alternative embodiments the recirculator 24 may be an optical fiber coupler.

Figure 5:
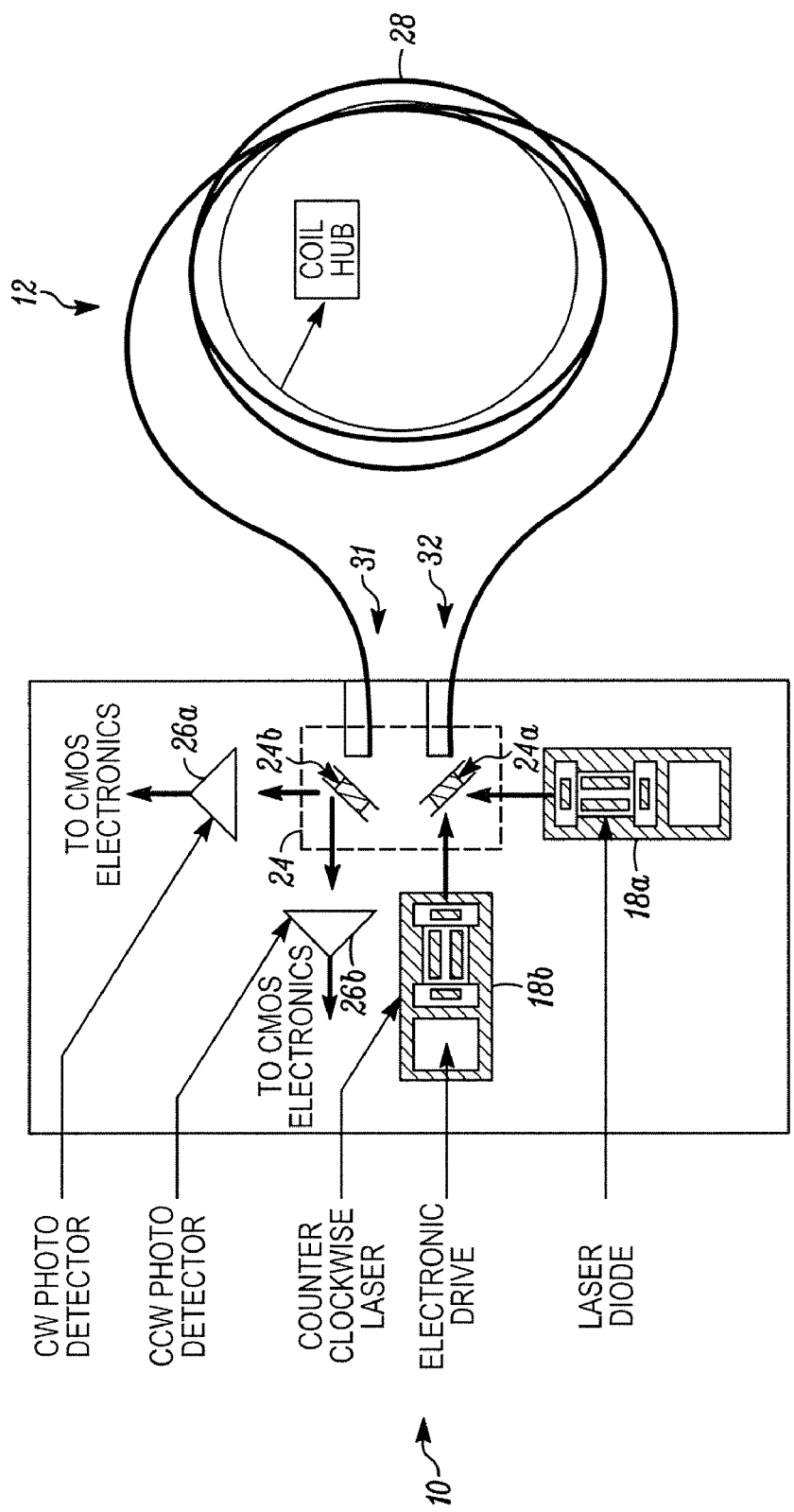
FIG. 5 is an expanded diagram of the sensor of FIG. 1.

FIG. 5 is a somewhat more complex version of FIG. 1 wherein the light may be circulated in either the clockwise (CW) or counterclockwise (CCW) direction. In FIG. 5, the recirculator 24 has been broken into two mirrors 24a and 24b that function substantially the same as the mirror 24 of FIG. 1. For purposes of simplicity, the discussion below will be directed primarily to FIG. 1.

In an exemplary embodiment, the light source 18 is a tunable laser having frequency stability, a relatively narrow linewidth, and a relatively high power capability. The light source 18 is tuned through, a frequency region that corresponds with the resonance frequency $f_o$ of the resonator 12 in either the CW or the CCW direction. In general, the recirculator 24 may be any optical element that reflects and reintroduces light emerging from one end of the optical fiber coil 28 into the other end of the fiber coil 28, thus causing light to propagate through the optical fiber coil 28 many times. The use of an input mirror instead of a fiber optic coupler for the recirculator 24 is one advantage of the sensor 10 since the mirror may be used to attenuate polarization errors and other error mechanisms, and may introduce few imperfections.

In one case, the optical fiber coil 28 is made of fiber whose core is typically glass based and with a cladding 29 surrounding the core. An optical fiber having an extremely low bend loss is preferably used, and the optical fiber coil 28 preferably has a relatively large number of turns about a substantially small area. For example, the coil 28 may have from about 20-40 turns of the optical fiber about a one centimeter diameter. Generally, the longer the optical path, such as provided by the optical fiber coil 28, the greater the signal-to-noise ratio of the sensor 10. To improve the signal-to-noise ratio of the sensor 10, the optical path may be increased by increasing the number of turns of the optical fiber coil 28. In the optical fiber coil 28, light introduced by the recirculator 24 traverses mostly inside the core, and only about a few percent of the optical energy of light enters the cladding of the optical fiber.

The cladding 29 is a functional coating which changes in absorbance or refractive index when exposed to a specific chemical contaminant. The cladding 29 may be made of a polymer having the characteristic of a high fractional free volume. A polymer with a high fractional free volume means that these polymers have chains which are designed not to pack closely together, leaving voids or empty regions which can be at least partially filled by other compounds, or are microporous in addition to having a high fractional free volume.

In one embodiment of the present invention, the polymer preferably has voids or empty regions of the polymer structure in which the spacings between adjacent polymer molecules vary between zero and about 10 Angstroms. Preferable polymers having such regions are high factional free volume polysulfones, polyimides, polyphenyl ethers and polycarbonates, which have polymer backbones with rigid sections that do not crystallize well. This means that within the structure there are empty regions which might be filled with a substrate or contaminant. However, these polymers do not have pores and therefore are not porous, since they do not have channels leading from a surface into the interior. Polyimides of this type which are believed to be useful in this invention are disclosed in U.S. Pat. No. 5,248,319 issued to Ekiner et. al, and by Y. Hirayama, et. al in an article entitled "Relation of Gas Permeability With Structure of Aromatic Polyimides I" in the *Journal of Membrane Science* 111 (1996) 169-182.

Particularly preferred polymers as described in this embodiment which is believed to be useful as the cladding 29 or as a coating thereof are polyimides having the aforesaid properties. Polyimide polymers as described can be prepared from a dianhydride and a diamine, and wherein the diamine and the dianhydride can have two or more different aromatic structures. Particularly preferred polyimide polymers can be prepared from a diaminophenyl methane or a diaminophenyl ether. Preferred polyimide polymers for this purpose are believed to have repeating units of:

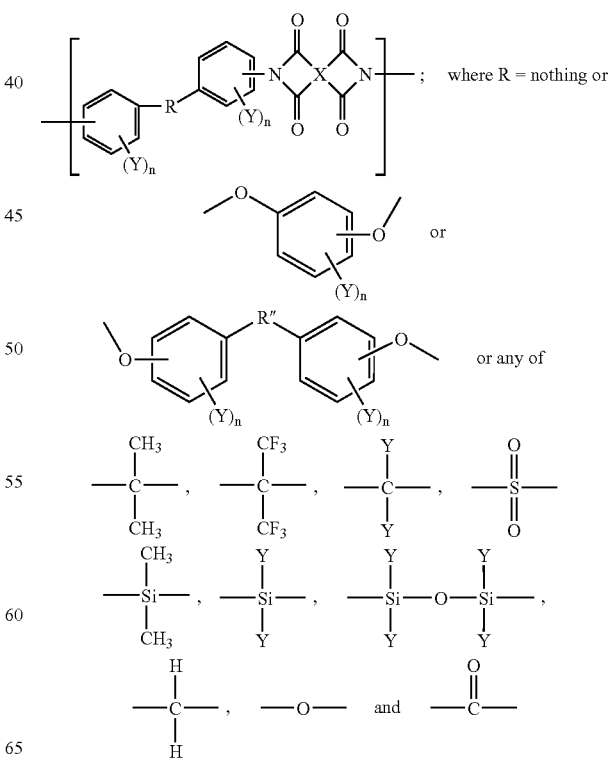

or mixtures thereof, where X is selected from the group consisting of

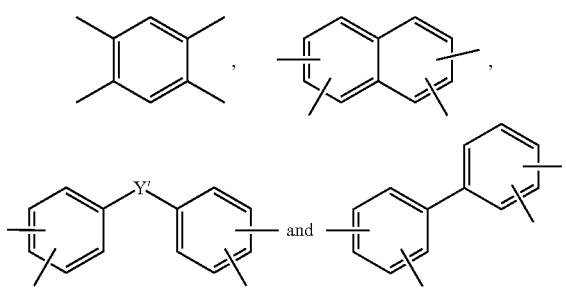

and mixtures thereof; Y is selected from the group hydrogen, alkyl groups having 1-6 carbon atoms, aromatic groups having 6-12 carbon atoms and halogen, where n is an integer from 0 to 4; where Y' is selected from the group consisting of

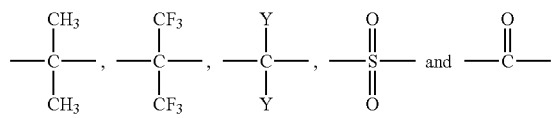

or mixtures thereof; and where R" is selected from the group consisting of

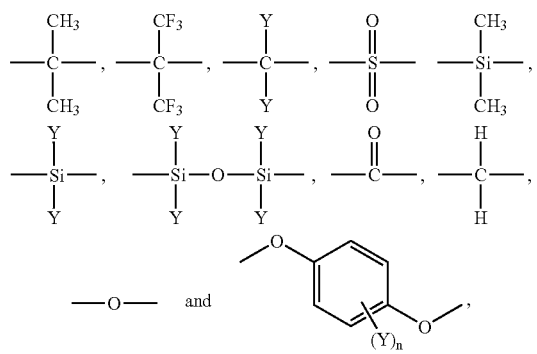

and mixtures thereof.

Such polymers as described above are believed to be well suited for use with the sensor 10 because they can be applied using conventional polymer coating techniques, and will sorb and concentrate organic contaminants selectively. Sorption will result in a change in the refractive index of the polymer. Additionally, specific functional indicators may be incorporated into such polymers to add an absorption-based indicator of the presence of a contaminant.

In another embodiment of the present invention, the cladding 29 may be made of a polymer which is microporous, i.e. is considered as a polymer of intrinsic microporosity (PIMs). These polymers may have pores of from about 4 to about 6 Angstroms, and preferably comprise organic macromolecules comprised of first generally planar species connected by rigid linkers having a point of contortion such that two adjacent first planar species connected by the linker are held in non-planar orientation. Polymers of this type which are believed to be useful in this invention are disclosed in International Published Application No. WO 2005/113121, to The University of Manchester, Manchester, U.K., published Dec. 1, 2005.

More preferably, the microporous polymer comprises organic macromolecules comprising repeating units having the formula:

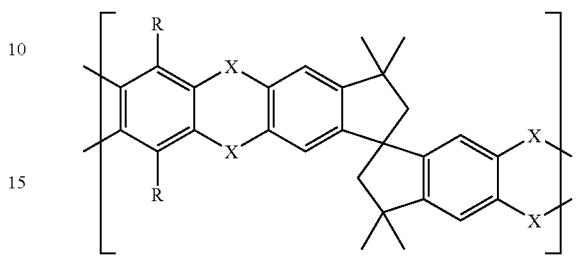

wherein X is O, S or N-Q; where R is H or alkyl having 1-6 carbon atoms or —CN, and Q is H, methyl or ethyl.

It will be understood by those skilled in the art that, in order to guide light inside the fiber, the refractive index of the cladding must be less than that of the core fiber itself. The refractive index of the cladding will be a function of its chemical structure, and also of its fractional free volume. Depending on the choice of the fiber core material, only those cladding materials with refractive indices compatible with that choice will be desirable.

In operation, light produced by the light source 18 is directed to the first mirror reflector 20 which in turn directs this light to the recirculator 24. Light from the light source 18 is scanned (swept) through the resonance frequency of the resonator (which is comprised of the optical fiber coil 28 and the recirculator 24), in a corresponding direction (e.g., the clockwise direction) of propagation, a first portion of which is transmitted through the recirculator 24 and into the first end 31 of the optical fiber coil 28. A second portion, i.e. the reflected portion, is reflected from the recirculator 24 to mirror 22. The resonance frequencies for each of the CW and CCW paths through the optical fiber coil 28 are based on a constructive interference of successively circulated beams in each optical path. After the first portion of light propagates through the core of the optical fiber coil 28, the light emerges from the second end 32 of the optical fiber coil 28. In this exemplary embodiment, the light emerging from the second end 32 is directed to the recirculator 24. A portion of this light is reflected back into the first end 31, by the recirculator 24 while another portion is transmitted (i.e., the transmitted wave) to the second mirror reflector 22. The transmitted wave is a fraction of (and is derived from) the recirculating light wave inside the resonator 12. The transmitted wave and the reflected wave are directed, via the second mirror reflector 22 to the photodetector 26 where they are interfered (i.e., interference occurs between the transmitted and reflected waves). As the frequency of the light is detuned well away from resonance, the transmitted portion is very small and only the reflected portion impinges on the photodetector, indicating a maximum intensity, and very little destructive interference. As the frequency is scanned through the center of the resonance, the transmitted wave is maximized, producing maximum destructive interference with the reflected wave, and therefore providing a resonance dip whose minima is indicative of the resonance center.

To observe the resonance center-frequency of the resonator (consisting of optical fiber coil 28 and recirculator 24) 12, in either the CW or CCW direction, the light intensity detected by the photodetector is measured or a standard detection technique may be used. Detection may be accomplished synchronously by sweeping the light source 18 through a frequency range while synchronously detecting a light output via the photodetector 26. In the case of synchronous detection, the input light beam is sinusoidally frequency modulated by the controller 16 at a frequency ($f_m$) to dither the input beam frequency across the resonance lineshape while resonance is measured by the photodetector 26. For example, the electronic module 16 may sweep the input light beam across a frequency range via a controlling signal to the light source 18 while demodulating the output of the photodetector 26 at $f_m$ to measure the resonance center and/or the resonance width via the light output of the circulating light beam. At a line center of the resonance lineshape, or the resonance center, the photodetector 26 detects a minimum output at the fundamental detection frequency $f_m$ and detects a maximum on either side of the lineshape substantially where the slope is highest. When the frequency is off-resonance, an intensity signal maximum is observed, but the signal at $f_m$ is substantially zero. To observe the linewidth of the resonance lineshape, the laser frequency is scanned such that the light intensity signal of the photodetector 26 at least goes through a sequence of observing a half maximum, then the minimum, then another half maximum, all as the laser frequency is scanned monotonically (i.e., swept through the frequency range of resonance at $f_o$).

Alternatively a measure of the lineshape width may be determined by monitoring the frequency difference between maximum amplitudes of the demodulated signal at $f_m$, as the laser frequency is scanned monotonically. In this case, a measurement of the frequency width of the resonance between points of highest slope is proportional to the resonator linewidth, and thus the loss of the resonator. The laser frequency excursion from half-maximum to half maximum of intensity is the resonator linewidth (or proportional to the resonator linewidth), which is indicative of the loss change within the fiber coil 28, and hence, is a measure of the presence of a chemical substance that alters the fiber attenuation. Widening of the linewidth represents the presence of the subject substance. The laser frequency excursion is measured by recording the laser frequency difference between the time that the detector observes a first half-maximum signal and the time the detector observes the second half-maximum signal. The laser frequency at each of those two points in time may be measured directly or indirectly. One direct measure involves beating its frequency with another laser that is not being scanned and measuring the beat frequency difference between the two points in time. An indirect, and perhaps less expensive way is to precalibrate the laser frequency versus the electrical signal input used to scan the laser. The calibrated values may be saved in a lookup table 11 within a memory of the controller 16. This may be a current drive signal that changes the injection current of the laser, a current drive signal to a thermo-electric cooler that changes the temperature of the laser, or a voltage drive signal to a piezoelectric transducer that changes the pathlength of the laser cavity to change its frequency. In either of these cases, the laser frequency shift versus the magnitude of the drive signal can be factory-calibrated, which allows the drive signal excursion to be used as a measure of the frequency excursion during operation. Alternatively, as may be recognized by one skilled in the art, the laser frequency may be held fixed and the fiber resonator resonance frequency may be modulated and swept via actively stretching the fiber within the fiber resonator.

When the light source 18 is tuned away from the resonance frequency of the resonator 12 in the CW direction, for example, the energy from the CW beam does not enter the optical fiber and the light is reflected off the highly reflective mirror of the recirculator 24 to produce a maximum intensity at the photodetector 26. When the light source 18 is tuned at the resonance frequency of the resonator 12 in the CW direction, the CW beam energy enters the optical fiber coil 28, and the light striking the photodetector 26 has a minimum output thereby indicating the resonance center. Similarly, if the device were to inject light into the CCW direction instead, the energy of the CCW beam enters the optical fiber coil 28 when the CCW beam is tuned to the resonance frequency of the resonator 12 in the CCW direction.

When the chemical agent 30 is present within the optical fiber coil 28, the chemical agent is sorbed into the cladding. Sorbtion results in a change in the refractive index of the cladding. For example the altered optical properties of the optical fiber coil 28 include, but are not necessarily limited to, a change in the index of refraction or an increase or decrease in the optical attenuation of the optical fiber coil 28.

In order to scan the resonant frequency of the resonator 12, a driver controller 13 may sequentially select a predetermined set of laser diode 18 current values relating to scanning through the resonance frequency or multiple resonance frequencies. For example, the resonator 12 in an uncontaminated state may have half maximum optical energy output values (as measured by the diode 26) at resonant frequency values equal to $f_o+/-\Delta f$, and with the chemical contaminant the half maximum resonant frequency values may be $f_o+/-5\Delta f$. In this case, the predetermined set of current values would have a maximum current value $x_1$ and a minimum current value $x_2$ that correspond to $f_o+5\Delta f$ and $f_o-5\Delta f$, respectively. If the driver controller 13 where to step from the minimum current value to the maximum current value in twenty equal steps then the first current value applied to the laser diode 18 would be $x_2$ and the increment in current value for each step would be $(x_1-x_2)/20$. In this case, the first current value would be $x_2$, the second value would be $x_2+(x_1-x_2)/20$, the third value would be $x_2+2(x_1-x_2)/20$, and so on. Another possibility is that the laser current (the frequency too) is scanned from $X_2$ to $X_1$ in an "analog", or continuous way, and the points of maximum slope are detected at $X_L$ and $X_H$, the linewidth is then proportional to $X_L-X_H$ and this may be measured over time to monitor attenuation produced by presence of the chemical agent. In the case of a sensor based on an index change, the above technique may also be applied but the values $X_L$ and $X_H$ are recorded at line centers of two different resonances, producing a measurement of the free spectral range. The presence of the chemical agent that changes the refractive index experienced by the light alters the free spectral range.

The one-half maximum values on either side of resonant frequency $f_o$ may be detected by the photodetector 26 and correlated to light source current values. In this case, the predetermined set of current values may extend over some larger current range determined by the changes to the resonant frequency caused by the presence of the chemical material. If the change in resonant frequencies caused by the presence of the chemical material causes one-half maximum values of the resonant frequency $f_o$ to spread out by a factor of five, then the predetermined current range may correspond to 5 times the one-half maximum values of the resonator 12 in the uncontaminated state.

In one illustrated embodiment, the lookup table 11 may contain a list of current values and the respective frequencies that corresponds to those current values. The lookup table 11 may also contain a number of frequency signatures. A frequency signature in this case means a set of frequencies of the light source 18 and a corresponding value that is to be detected by the photodetector 26. A first reference signature may be provided within the lookup table 11 for the resonator in an uncontaminated state and one or more other contamination or chemical agent signatures may be provided within the lookup table 11 for the resonator 12 in the contaminated state. In use, the controller 16 continually collects test signatures by causing the light source 18 to scan through the predetermined set of frequencies while collecting a respective light value from the photodetector 26. The test signature is compared with the reference and contamination signatures within a comparator 15. When the comparator 15 detects a match between the test signature and a contamination signature, the controller 16 activates an alarm.

In an exemplary embodiment, the sensor 10 is constructed on a silicon-based micro-optical bench 14 that integrates electronics (e.g., the electronic module 16) and optics and provides an efficient and expedient interface between the two. Miniature optical components having a feature size of as little as 10 microns, such as the mirror reflectors 20, 22 and the recirculator 24, may be mounted on silicon surfaces to eliminate large bulk optics, even though the light wave may be traveling in free space. Some of these optical functions may also be embedded in waveguides residing in the silicon material. In this exemplary embodiment, the light source 18 and related frequency tuning components and the photodetetctor 26 may also be mounted on the optical bench. The use of these techniques allows the fabrication of optics in or on a silicon platform and thus integrated of the optics with the electronics. The light source itself may be a compound structure on which several components may be mounted, or formed on the micro-optical bench 14. For instance, it may be an external cavity laser diode, where the laser diode is placed between two reflective surfaces which are either formed or placed on the substrate. There may also be frequency selective intra-cavity elements formed or placed within the laser cavity to make it a single frequency laser, such as a grating or an etalon. There may also be elements included with laser source 18 that are mounted or formed external to the laser cavity that are used to shape or collimate the laser beam, such as lenses.

Figure 2:
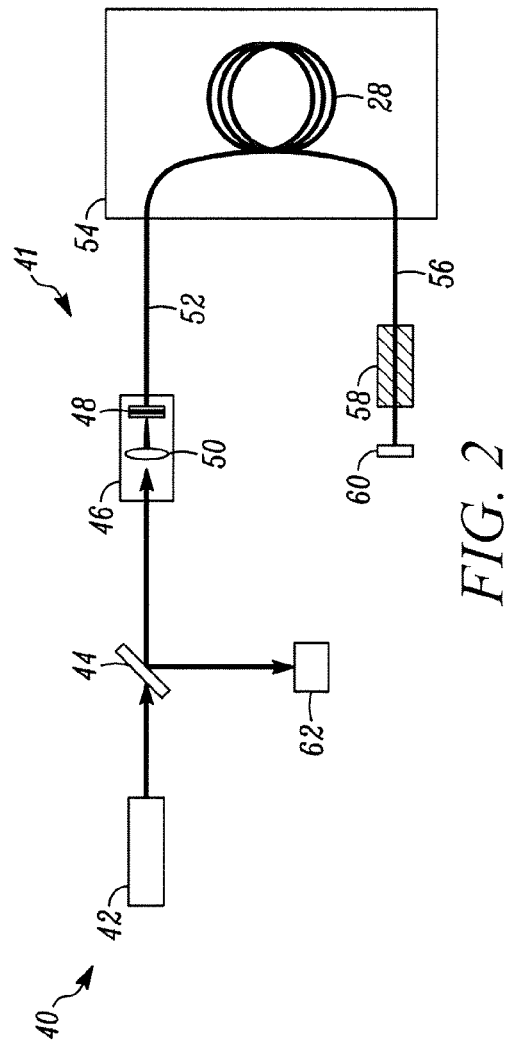
FIG. 2 is a schematic diagram of a chemical agent sensor having a linear resonator in accordance with another exemplary embodiment of the present invention.

FIG. 2 is a schematic diagram of a chemical agent sensor 40 having a linear resonator 41 in accordance with another exemplary embodiment of the present invention. The sensor 40 comprises a tunable laser (e.g., a He—Ne laser, or an external cavity laser diode) 42 that synthesizes an input light beam and introduces the input light beam into the linear resonator 41. The sensor 40 comprises a beam splitter (e.g., a 50-50% beam splitter) 44, an input element 46, the optical fiber coil 28, and output mirror 60, and a photodetector 62. the input element 46 includes, but is not necessarily limited to, an input mirror 48 (e.g., a 95-5% mirror) although a fiber grating may be substituted for the input mirror 48. Additionally, the input element 46 may include optics 50 for directing the light from the beam splitter 44 to a first end 52 of the optical fiber coil 28 and for directing light from the same end 52 of the optical fiber coil 28 to the beam splitter 44. The optical fiber coil 28 is housed in a permeable package 54 for detecting the predetermined chemical agent (e.g., associated with the fiber coating chemistry in the optical fiber coil 28). The linear resonator 41 is formed by reflector 48, fiber coil 28 and reflector 60. Reflectors 48 and 60 may be formed or deposited directly onto the fiber tips or fiber ends 52 and 56 to achieve a low loss resonator.

A modulator (e.g., a piezoelectric transducer) 58 may be coupled to the optical fiber coil 28 to modulate the pathlength of the light (e.g., sinusoidal modulation) circulating through the optical fiber coil 28 during resonance linewidth determination so that synchronous detection may be used. For example, the input light beam produced by the laser 42 is scanned through the resonance frequency $f_o$ of the resonator and the modulator 58 sinusoidally modulates the pathlength of the light circulating through the optical fiber coil 28. In another exemplary embodiment, the modulator 58 is omitted when the laser 42 has frequency modulation capabilities incorporated therewith. In a third exemplary embodiment, the laser frequency is fixed, and both the frequency scanning an the modulation are effected by the modulator 58. In this latter case, the resonator resonance frequency is scanned through the region of the laser frequency, which is equivalent, in principle, to scanning the laser frequency across a fixed resonance frequency of the fiber resonator.

The input light beam from the laser 42 is directed by the beam splitter 44 to the input element 46 which directs the input light beam to the first end 52 of the optical fiber coil 28. When tuned to the resonance frequency associated with the resonator 41 containing the optical fiber coil 28, a majority of the input light beam enters the optical fiber coil 28. After propagating through the optical fiber coil 28, light emerges from the second end 56 of the optical fiber coil 28 and impinges on the output mirror 60 which reflects the light back into the optical fiber coil 28 at the second end 56. A light output is produced from the light propagating back and forth in the optical fiber coil 28 at the first end 52 of the optical fiber coil 28 which is directed by the input element 46 to the beam splitter 44. The beam splitter 44 reflects a portion of the light output to the photodetector 62, which may be coupled to electronics (similar to FIG. 1).

Figure 3:
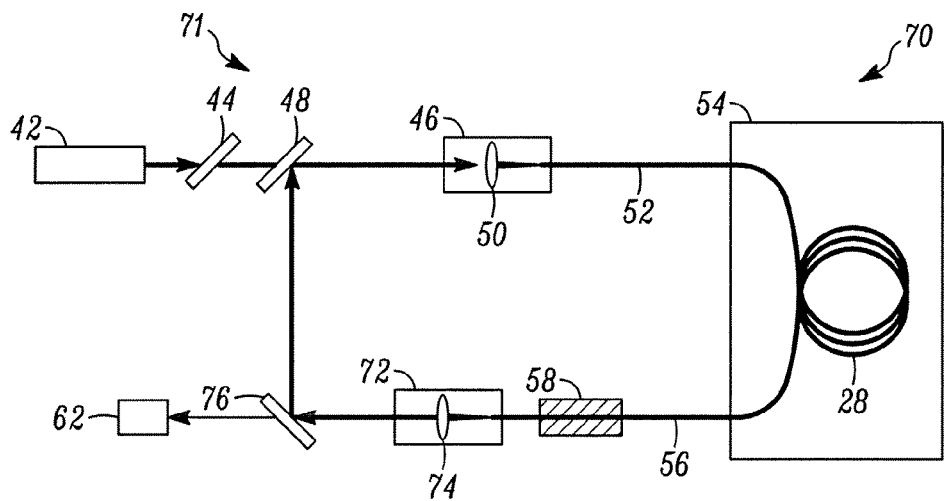
FIG. 3 is a schematic diagram of a chemical agent sensor having a ring resonator in accordance with another illustrated embodiment of the invention.

FIG. 3 is a schematic diagram of the chemical agent sensor 70 having a ring resonator 71 in accordance with another exemplary embodiment of the present invention. In this exemplary embodiment, the laser 42 introduces the input light beam into the ring resonator 71. The chemical agent sensor 70 comprises a laser 42, a beam splitter 44, the input mirror 48, an input element 46, the optical fiber coil 28, an output element 72, an output mirror 76, and a photodetector 62. The optical fiber coil 28 is housed in the permeable or semi-open package 54, and the modulator (e.g., a piezoelectric transducer) 58 may be coupled to the optical fiber coil 28 to modulate the light path (e.g., sinusoidal modulation and/or resonance frequency scanning) circulating through the optical fiber coil 28 during resonance linewidth determination or free spectral range determination. The resonator comprises, at mirror 48 and 76, a fiber coil 28, input element 46 and output element 72. In another embodiment, mirrors 48 and 76 are designated with sufficient curvature to eliminate input element 46 and output element 72. In yet another embodiment the two mirrors 48 and 76 and the input element 46 and output element 72 are replaced with a fiber optic coupler which is spliced to the coil 28, or are replaced by two fiber optic couplers which are spliced to each other and the coil.

The input light beam from the laser 42 is directed to the input mirror 48 which transmits a portion of the input light beam to the input element 46. The input element 46 directs light form the input mirror 48 to the first end 52 of the optical fiber coil 28. When tuned to the resonance frequency of the resonator, a majority of the input light beam enters the first end 52 of the optical fiber coil 28. After propagating through the optical fiber coils 28, light emerges from the second end 56 of the optical fiber coil 28 and is directed to the output element 72. The output element 72 may include optics 74 for directing light from the second end 56 of the optical fiber coil 28 to the output mirror 76. The output mirror 76 reflects the light from the output element 72 to the input mirror 48, and input mirror 48 directs a majority of this to the input element 46 to complete the resonator optical path. A light output is produced from the light circulating around the optical path, including the optical fiber coil 28, at the output mirror 76 which passes a small fraction of the light that is circulating within the resonator out to the photodetector 62.

Figure 4:
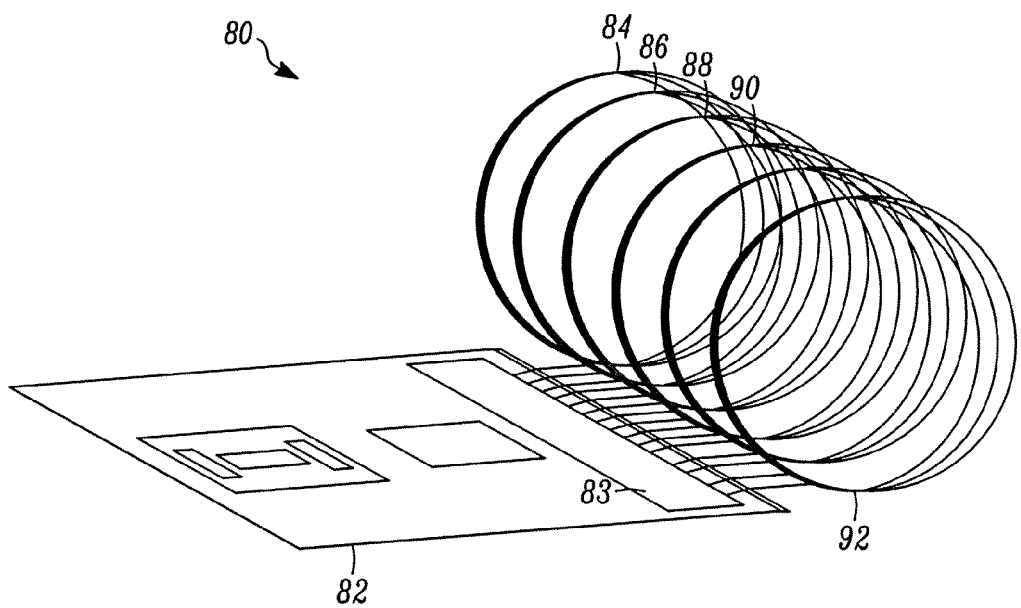
FIG. 4 is a schematic diagram of a multiplexed chemical agent sensor in accordance with an illustrated embodiment of the invention.

FIG. 4 is a schematic diagram of a multiplexed chemical agent sensor 80 in accordance with another exemplary embodiment of the present invention. The sensor 80 comprises a silicon-based micro-optical bench 82 and a multiple optical fiber coils 84, 86, 88, 90, 92 coupled to the micro-optical bench 82. The micro-optical bench 82 integrates electronics (e.g., the electronics module 16 shown in FIG. 1) and optics (e.g., the beam splitter 44, input and output mirrors 48, 60, 76, input and output elements 46, 72, and photodetector 62 shown in FIGS. 2 and 3). For example, the electronics module 16, photodetector 26, light source 18, mirror reflectors 20, 22, and input mirror 24 shown in FIG. 1 may be integrated with, or mounted on, the micro-optical bench 82. The sensor 80 additionally includes, but is not necessarily limited to, a multiplexer 83 formed on the micro-optical bench 82 is coupled (e.g., via one or more fiber vee-grooves and/or input mirrors) to each of the optical fiber coils 84, 86, 88, 90, 92.

In the exemplary embodiment, the multiplexer 83 directs input light beams to each of the optical fiber coils 84, 86, 88, 90, 92 and receives output light beams from the optical fiber coils 84, 86, 88, 90, 92 having circulated through each of the optical fiber coils 84, 86, 88, 90, 92. The output light beams are each directed to one or more input mirrors to produce a light output, from which a resonance lineshape may be determined, and may be directed back to the corresponding optical fiber coil to complete a resonator optical path. The input light beams are each scanned across the resonance frequency or resonance frequencies of the corresponding optical resonator containing each of the optical fiber coils 84, 86, 88, 90, 92. As previously described, this may be accomplished by having a fixed average input light frequency and scanning the length of each of the resonator pathlengths, thus scanning through the resonance lineshape or lineshapes. Each of the optical fiber coils has coating on the fiber that makes it sensitive to different chemical agents. Using the sensor 80, multiple chemical agents may be detected using a single device with a common output interface and possibly a wireless transmitter.

A specific embodiment of a chemical detector has been described for the purpose of illustrating the manner in which one possible alternative of the invention is made and used. It should be understood that the implementation of other variations and modifications of embodiments of the invention and its various aspects will be apparent to one skilled in the art, and that the various alternative embodiments of the invention are not limited by the specific embodiments described. Therefore, it is contemplated to cover all possible alternative embodiments of the invention and any and all modifications, variations, or equivalents that fall within the true spirit and scope of the basic underlying principles disclosed and claimed herein.

The invention claimed is:

1. A chemical detector for detecting predetermined chemicals comprising:
   an optical resonator containing an optical fiber;
   a polymer having a high fractional free volume higher than about 0.1, cladding the optical fiber;
   a coherent light source that excites the optical fiber; and
   a chemical signature detector that detects a predetermined chemical based upon either a change in a resonance lineshape or a change in free spectral range of the optical fiber resonator caused by absorption of the predetermined chemical into the high fractional free volume polymer cladding of the fiber.

2. The chemical detector as in claim 1 wherein the coherent light source further comprises a distributed feedback (DFB) laser diode.

3. The chemical detector as in claim 2 wherein the chemical signature detector further comprises a photo-diode.

4. The chemical detector as in claim 3 wherein the chemical signature detector further comprises a laser controller coupled to the DFB laser that sweeps a junction current of the DFB laser through a predetermined current range.

5. The chemical detector as in claim 4 wherein the chemical signature detector further comprises a laser look up table that correlates current values of the predetermined current range with lasing frequencies of the DFB laser.

6. The chemical detector as in claim 5 wherein the laser lookup table further comprises a first junction current value differences that corresponds to a calibration value and to either a resonance linewidth or a free spectral range of the optical fiber resonator before being exposed to any chemicals.

7. The chemical detector as in claim 6 wherein the chemical signature detector further comprises a chemical signature look up table that contains a resonant frequency signature value for at least some of the predetermined absorbed dosages of a chemical.

8. The chemical detector as in claim 7 wherein the chemical signal detector further comprises a comparator that detects a resonance of the optical fiber by comparing an output of the photo-diode with a resonance threshold value.

9. The chemical detector as in claim 7 wherein the chemical signature detector further comprises frequency modulation of the coherent light and subsequent demodulation of the photo-diode output to determine the resonance width of the optical resonator, or the free spectral range.

10. The chemical detector of claim 9 wherein the polymer cladding has empty regions within the polymer structure wherein the spacings between adjacent polymer molecules vary between zero and about 10 Angstroms and which are capable of being at least partially filled with a predetermined chemical to be detected.

11. The chemical detector as in claim 10 wherein the polymer with a high fractional free volume is selected from the group consisting of high fractional free volume polysulfones, polyimides, polyphenyl ethers and polycarbonates, which polymers have a fractional free volume higher than about 0.1, and are capable of cladding the fiber.

12. The chemical detector as in claim 11 wherein the polymer is a polyimide polymer having a fractional free volume higher than about 0.1 and is capable of cladding the fiber.

13. The chemical detector as in claim 12, wherein the polymer is a polyimide prepared from a dianhydride and a diamine selected from the group consisting of a diaminophenyl methane and a diaminophenyl ether.

14. The chemical detector as in claim 13, wherein the polymer is a polyimide having repeating units of

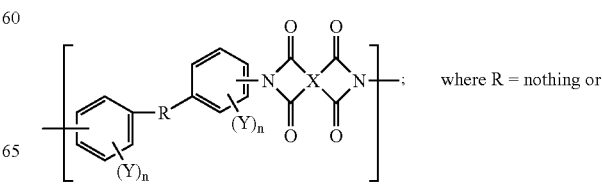

-continued

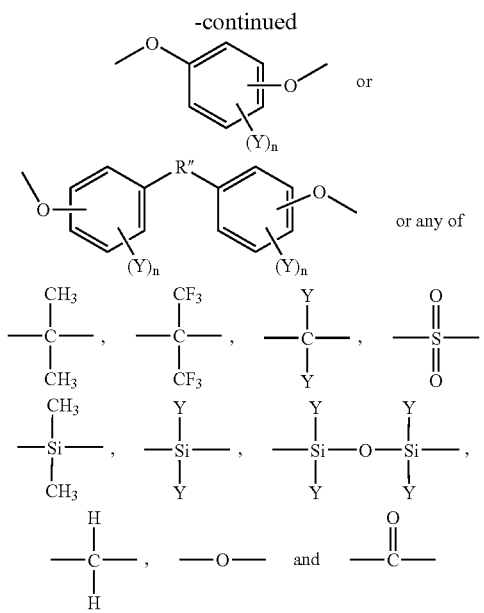

or mixtures thereof, where X is selected from the group consisting of

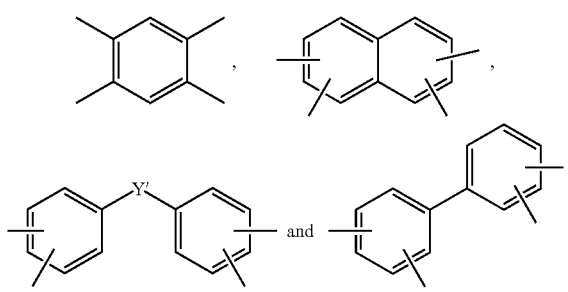

and mixtures thereof, Y is selected from the group hydrogen, alkyl groups having 1-6 carbon atoms, aromatic groups having 6-12 carbon atoms and halogen, where n is an integer from 0 to 4; where Y' is selected from the group consisting of

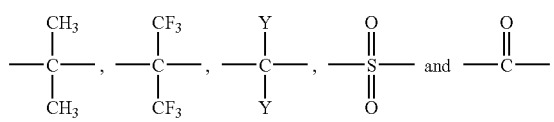

or mixtures thereof; and where R" is selected from the group consisting of

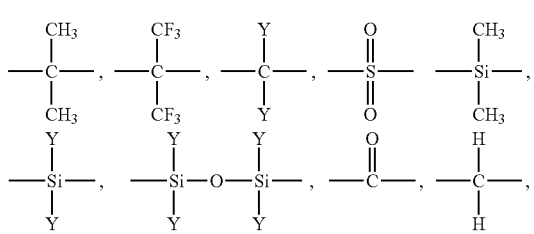

-continued

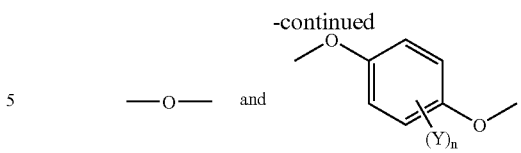

and mixtures thereof.

15. Chemical detector as in claim 13 wherein the polyimide is prepared from 4,4'-(hexafluoroisopropylidene)diphthalic anhydride and a diaminophenyl compound selected from the group consisting of a 4,4'-diaminophenyl methane and a 4,4'-diaminophenyl ether.

16. A chemical detector for detecting predetermined chemicals comprising:
   an optical fiber arranged as an optical fiber resonator;
   a microporous polymer having a high fractional free volume higher than about 0.1 cladding the optical fiber;
   a coherent light source that excites the optical fiber resonator; and
   a chemical signature detector that detects a predetermined chemical based upon a change in a resonance characteristic of the optical fiber resonator caused by absorption of the predetermined chemical into the high fractional free volume polymer cladding of the fiber.

17. The chemical detector as in claim 16 wherein the microporous polymer comprises organic macromolecules comprised of first generally planar species connected by rigid linkers having a point of contortion such that two adjacent first planar species connected by the linker are held in non-planar orientation.

18. The chemical detector as in claim 17 wherein the microporous polymer comprises organic macromolecules comprising repeating units having the formula:

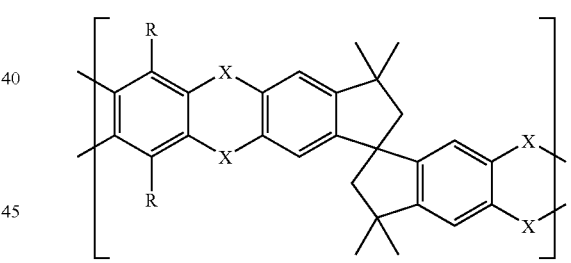

wherein X is O, S or N-Q; where R is H or alkyl having 1-6 carbon atoms or —CN, and Q is H, methyl or ethyl.

19. A method for detecting a set of predetermined chemicals comprising:
   providing optical fibers, each arranged as optical fiber resonators, each having a polymer having a high fractional free volume higher than about 0.1, cladding the optical fiber;
   a coherent light source exciting the optical fiber resonators; and
   a chemical signature detector detecting a set of predetermined chemicals based upon a change in a resonance characteristic of the optical fiber resonators upon the light source exciting the optical fiber resonators, caused by absorption of the predetermined chemical into the high fractional free volume polymer cladding of the fiber.

* * * * *